(12) United States Patent
Levine

(10) Patent No.: US 7,201,577 B2
(45) Date of Patent: Apr. 10, 2007

(54) TOOTH WHITENER APPLICATOR AND METHOD

(75) Inventor: Jonathan B. Levine, New York, NY (US)

(73) Assignee: GoSmile, Inc., New York, NY (US)

( * ) Notice: Subject to any disclaimer, the term of this patent is extended or adjusted under 35 U.S.C. 154(b) by 19 days.

(21) Appl. No.: 10/128,291

(22) Filed: Apr. 24, 2002

(65) Prior Publication Data

US 2003/0203338 A1 Oct. 30, 2003

(51) Int. Cl.
*A61C 17/00* (2006.01)

(52) U.S. Cl. .................................. 433/215; 433/80

(58) Field of Classification Search ............... 433/215, 433/80, 89, 216, 141; 401/132, 133, 196, 401/183, 184; 222/93, 206; 206/209; 15/167.1; 132/308, 311
See application file for complete search history.

(56) References Cited

U.S. PATENT DOCUMENTS

| | | | | |
|---|---|---|---|---|
| 3,614,245 A | * | 10/1971 | Schwartzman | 401/132 |
| 4,106,652 A | * | 8/1978 | Leclabart | 215/253 |
| 4,441,227 A | * | 4/1984 | d'Argembeau | 15/167.1 |
| 4,572,689 A | * | 2/1986 | Chernack | 401/132 |
| 4,844,641 A | * | 7/1989 | Grosfilley et al. | 401/176 |
| 4,875,602 A | * | 10/1989 | Chickering et al. | 222/187 |
| 5,098,297 A | * | 3/1992 | Chari et al. | 433/215 |
| 5,310,563 A | * | 5/1994 | Curtis et al. | 424/616 |
| 5,928,611 A | * | 7/1999 | Leung | 422/131 |
| 6,001,380 A | * | 12/1999 | Smith et al. | 424/402 |
| 6,092,535 A | * | 7/2000 | Moore | 132/270 |
| 6,283,933 B1 | * | 9/2001 | D'Alessio et al. | 604/3 |
| 6,478,191 B1 | * | 11/2002 | D'Alessio et al. | 222/129 |
| 6,517,350 B2 | * | 2/2003 | Diasti et al. | 433/215 |
| 2002/0141949 A1 | * | 10/2002 | Banerjee et al. | 424/53 |
| 2003/0091516 A1 | * | 5/2003 | Pellico | 424/53 |

* cited by examiner

*Primary Examiner*—Melba Bumgarner
(74) *Attorney, Agent, or Firm*—H. Jay Spiegel

(57) ABSTRACT

An apparatus for practicing the inventive method includes a glass ampule having a tooth whitening solution vacuum sealed within a chamber of the ampule. The ampule is contained within a cylindrical plastic sleeve closed at one end and enclosed at its other open end by the proximal termination of a brush-type applicator. An adhesive such as glue is used to adhere the periphery of the brush to the inner surfaces of the plastic cylinder. The bristles preferably have circular cross-sections so that when they are tightly packed together and adhered to the plastic cylinder, interstices between adjacent bristles are sufficiently large enough to permit flow through of the tooth whitening composition while being sufficiently small enough to prevent shards of glass from the ampule, when broken open, to pass through the brush. A cardboard sleeve surrounds the plastic cylinder to protect the user from the glass ampule when broken. The method of using the inventive apparatus is also disclosed.

15 Claims, 1 Drawing Sheet

FIG. 1
FIG. 2
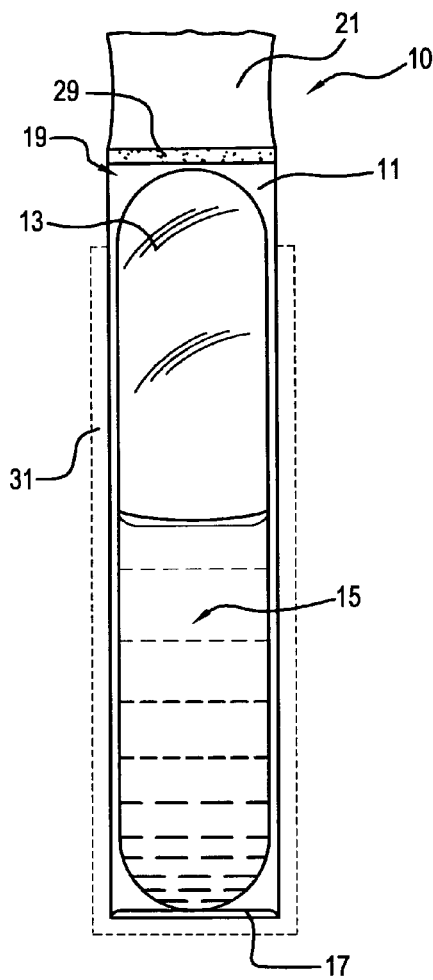
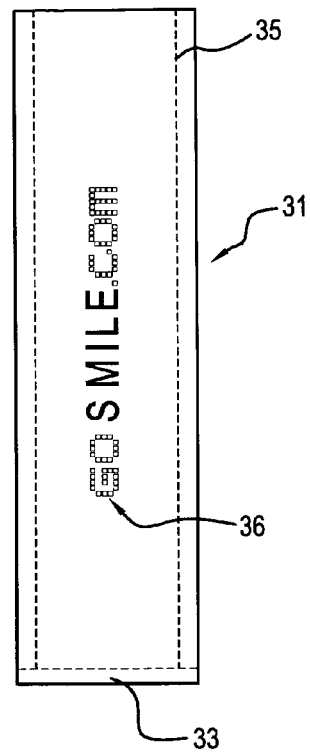
FIG. 3
FIG. 4
FIG. 5
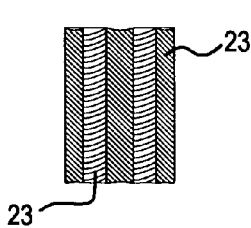
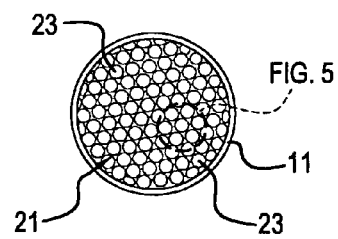
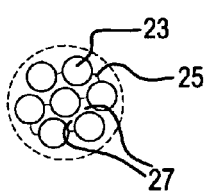

TOOTH WHITENER APPLICATOR AND METHOD

BACKGROUND OF THE INVENTION

The present invention relates to a tooth whitener applicator and method. In the prior art, it is known to whiten teeth using various well known tooth whitening compositions. However, the tooth whitening process is often cumbersome and messy. Most dentists offer services involving tooth whitening, however, for the average patient, it is expensive to have the dentist perform the whitening services. As such, a need has developed for a tooth whitening applicator that is both inexpensive and easy to use.

Applicant is aware of U.S. Pat. No. 5,098,297 to Chari et al. which discloses an apparatus for application of a tooth desensitizing composition. Chari et al. fail to teach or suggest tooth whitening and disclose the use of a swab-type applicator that retains and dispenses a tooth desensitizer onto the teeth. Chari et al. disclose a separate filter disc designed to prevent shards of glass from an ampule containing the desensitizing solution from escaping into the mouth of the patient. The present invention differs from the teachings of Chari et al. in several respects. First, the present invention contemplates application of a tooth whitening composition rather than a tooth desensitizing composition. Second, the present invention contemplates evacuating the interior of the glass ampule containing a monodose of the tooth whitening composition so that its shelf life is extended. Third, the present invention contemplates use of a brush to dispense the tooth whitening composition with the brush doubling as the filter preventing glass shards from entering the mouth of the patient. The tooth whitening composition is somewhat more viscous than the tooth desensitizing composition taught by Chari et al. Due to its increased viscosity, the wad-type applicator of Chari et al. would not be suitable for use in dispensing the tooth whitening composition of the present invention.

SUMMARY OF THE INVENTION

The present invention relates to a tooth whitener applicator and method. The present invention includes the following interrelated objects, aspects and features:

(1) In a first aspect, the present invention contemplates an apparatus for practicing the method thereof. The apparatus includes a glass ampule having a monodose of a tooth whitening solution vacuum sealed therein. The ampule is contained within a cylindrical plastic sleeve closed at one end and enclosed at its other open end by the proximal termination of a brush-type applicator. An adhesive such as glue is used to adhere the periphery of the brush to the inner surfaces of the open end of the plastic sleeve.

(2) The bristles preferably have circular cross-sections so that when they are tightly packed together and peripheral bristles are adhered to the plastic cylinder, interstices between adjacent bristles are sufficiently large enough to permit flow through of the tooth whitening composition while being sufficiently small enough to prevent shards of glass from the ampule, when broken open, to pass therethrough.

(3) A cardboard sleeve surrounds the plastic cylinder to protect the user from the glass ampule when broken.

(4) The bristles of the brush applicator are sized and configured to permit brushing between teeth into the tooth enamel. It is in these areas where stains often accrue, namely, the inter-proximal areas of the teeth. Thus, a brush rather than a wad is chosen due to its effectiveness with regard to the anatomy of the teeth that are being treated.

(5) The method of using the inventive apparatus is as follows:

(a) A tooth whitening solution such as, for example, hydrogen peroxide, is vacuum sealed within a glass ampule;

(b) The glass ampule is placed within a plastic cylinder having one end closed and the other end open;

(c) The open end of the plastic cylinder is sealed by the proximal end of a brush through the use of adhesive applied therebetween;

(d) The brush is provided with bristles that are tightly adjacent one another and have spaces therebetween permitting flow of tooth whitening composition therethrough;

(e) A protector preferably made of cardboard is placed over the plastic cylinder;

(f) When it is desired to use the inventive apparatus to whiten the user's teeth, the glass ampule is squeezed through the cardboard protector until it shatters, releasing the tooth whitening composition into the plastic cylinder;

(g) The tooth whitening composition flows between the bristles of the brush while the tightly packed bristles act as a filter preventing the shards of glass from the ampule from traveling therebetween;

(h) The cardboard protector is pulsated to dispense the tooth whitening composition through the bristles and the bristles are run over the teeth of the user particularly in the inter-proximal areas until the tooth whitening composition is completely applied to the teeth;

(i) The elevated viscosity of the tooth whitening solution allows it to adhere to the teeth, rather than running off of them, for a sufficient period of time so that the tooth whitening composition effectively operates to whiten the user's teeth;

(j) After a prescribed time period, the mouth is rinsed to rinse away the tooth whitening composition.

As such, it is a first object of the present invention to provide a tooth whitener applicator and method of applying tooth whitener.

It is a further object of the present invention to provide such an invention in which tooth whitening composition is vacuum sealed within a glass ampule.

It is a yet further object of the present invention to provide such an apparatus in which a brush with tightly packed bristles is used to dispense the tooth whitening composition onto the teeth.

It is a still further object of the present invention to provide such an apparatus wherein a cardboard sleeve is placed over a plastic cylinder enclosing the glass ampule.

It is a still further object of the present invention to provide a method of using the apparatus to whiten the user's teeth.

These and other objects, aspects and features of the present invention will be better understood from the following detailed description of the preferred embodiments when read in conjunction with the appended drawing figures.

BRIEF DESCRIPTION OF THE DRAWINGS

FIG. 1 shows a side view of the inventive applicator with the cardboard protector thereof shown in phantom.

FIG. 2 shows a side view of the cardboard protector with the internal chamber thereof shown in phantom.

FIG. 3 shows a side view of the applicator brush of the present invention.

FIG. 4 shows an end view of the brush applicator.

FIG. 5 shows a magnified view of a portion of the view of FIG. 4 to show further details.

SPECIFIC DESCRIPTION OF THE PREFERRED EMBODIMENTS

Reference is first made to FIG. 1 in which the apparatus of the present invention is generally designated by the reference numeral 10 and is seen to include a preferably cylindrical plastic sleeve 11 containing an ampule 13 preferably made of glass in which is vacuum sealed a measured quantity of tooth whitening solution 15, preferably a monodose of that solution. The tooth whitening solution may, if desired, consist of a composition of hydrogen peroxide having increased viscosity over the composition of hydrogen peroxide commonly sold by the bottle.

The plastic cylindrical sleeve 11 has a closed bottom 17 and is upwardly open at 19.

An applicator tip 21 is best seen in FIG. 4 to consist of a plurality of individual bristles 23 (see also FIG. 5) closely packed together and enclosed within the opening 19 of the plastic cylinder 11.

As seen in FIG. 5, the individual bristles 23 are interconnected by a wire-like connector 25 during the manufacturing process thereof and are packed together as shown in FIGS. 4 and 5, so that they include interstices 27 existing between respective adjacent bristles 23.

As seen in FIG. 1, a band 29 of glue extends about the inner periphery of the plastic cylinder 11 adjacent the opening 19 thereof and adheres the bristles 23 as shown in FIG. 4 so that they act to close the opening 19 except for the interstices 27. FIG. 3 shows a side view of individual bristles 23 packed together in accordance with the teachings of the present invention.

As seen in FIGS. 1 and 2, a protector 31 preferably made of cardboard or other soft flexible material encloses much of the plastic cylinder 11. For this purpose, the protector 31 has a closed bottom 33 and an upper opening 36 sized to closely receive the outer periphery of the plastic cylinder 11 therein. A logo 36 or other markings may suitably be printed on the protector 31.

In the operation of the apparatus 10, in the configuration shown in FIG. 1, the plastic cylinder 11 is squeezed through the protector 31 to break the ampule 11, thereby allowing exit therefrom of the tooth whitening solution 15. The protector 31 is squeezed, thereby compressing the plastic cylinder 11 and causing the tooth whitening solution 15 to exit the plastic cylinder by entering the interstices 27 of the applicator 21. The interstices 27 are small enough to preclude any glass shards from the ampule 13 from traveling through the applicator 21 and into the mouth of the user. The applicator 21 is run over the teeth of the user while the plastic cylinder 11 is being pulsated by rythmically squeezing the protector 31. Tooth whitening solution 15 is dispensed through the interstices between the bristles 23 and onto the teeth of the user. The brush is specifically designed to allow application of the tooth whitening solution 15 in the inter-proximal area of the teeth, namely, between adjacent teeth which is where stains typically accrue. The enhanced viscosity of the tooth whitening solution 15 precludes it from washing away until the user actively rinses their mouth. With the tooth whitening solution adhering to the enamel surfaces of the teeth, the teeth are whitened. After a prescribed time period, the mouth is rinsed to rinse away the tooth whitening solution after the teeth have been effectively whitened.

As such, an invention has been disclosed in terms of a preferred embodiment of the apparatus and a preferred sequence of steps in practicing the method of use thereof of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A method of whitening teeth including the steps of:
    a) providing a single-dose tooth whitening applicator including:
        i) an ampule containing a tooth whitening composition vacuum packed therein;
        ii) a flexible sleeve with a closed end and an open end defining an opening, said sleeve defining an internal chamber receiving said ampule, said sleeve having a substantially uniform cross-section throughout a length thereof including at said opening;
        iii) a brush having bristles closely packed together and defining narrow interstices between adjacent bristles, said bristles having proximal ends inserted within said opening;
    b) opening said ampule and releasing said tooth whitening composition;
    c) conveying said tooth whitening composition through said interstices;
    d) using said brush to apply said tooth whitening composition to teeth.

2. The method of claim 1, wherein said ampule is made of glass.

3. The method of claim 1, wherein said flexible sleeve is made of plastic.

4. The method of claim 3, further including the step of gluing said proximal ends of said bristles into said open end of said sleeve.

5. The method of claim 3, wherein said applicator has a protector receiving said sleeve therein.

6. The method of claim 3, wherein said conveying step includes the step of squeezing said sleeve.

7. The method of claim 1, wherein said bristles have circular cross-sections.

8. The method of claim 1, wherein said tooth whitening composition comprises hydrogen peroxide.

9. The method of claim 1, wherein said conveying step includes the step of squeezing said sleeve.

10. A single-dose tooth whitening applicator comprising:
    a) an ampule containing a single dose of a tooth whitening composition vacuum packed therein, a flexible sleeve with a closed end and an open end defining an opening, said sleeve defining an internal chamber receiving said ampule, said sleeve having a substantially uniform cross-section throughout a length thereof including at said opening;
    b) a brush having bristles closely packed together and defining narrow interstices between adjacent bristles, said bristles having proximal ends inserted within said opening;
    c) said tooth whitening composition being released from said ampule and dispensed by flowing through said opening and through said narrow interstices of said brush;

d) said brush being employed to apply said tooth whitening composition to a user's teeth, said tooth whitening composition as applied to a user's teeth being a same composition as said tooth whitening composition as initially contained within said ampule.

11. The applicator of claim 10, wherein said ampule is made of glass.

12. The applicator of claim 10, wherein said flexible sleeve is made of plastic.

13. The applicator of claim 10, wherein said bristles have circular cross-sections.

14. The applicator of claim 10, wherein said tooth whitening composition comprises hydrogen peroxide.

15. The applicator of claim 10, further including a protector made of cardboard and extending over said sleeve.

* * * * *